Figure 1:
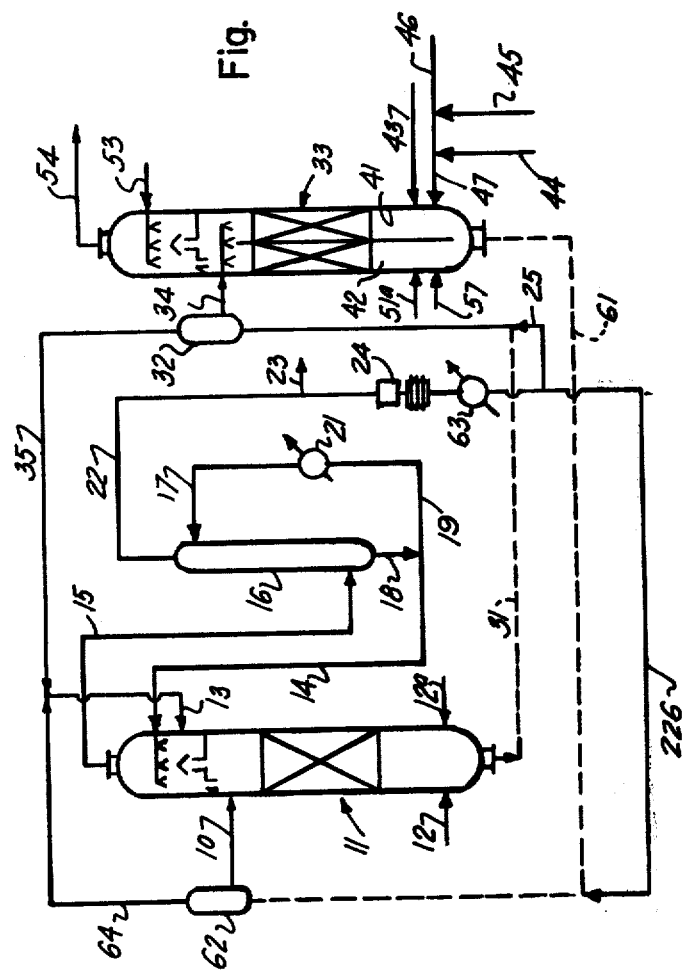

United States Patent [19]

Schindler

[11] 4,207,267
[45] Jun. 10, 1980

[54] DEHYDROCHLORINATION OF 1,2-DICHLOROETHANE

[76] Inventor: Harvey D. Schindler, 45 Berwyn Pl., Fairlawn, N.J. 07410

[21] Appl. No.: 564,456

[22] Filed: Apr. 2, 1975

Related U.S. Application Data

[63] Continuation of Ser. No. 437,985, Jan. 30, 1974, abandoned.

[51] Int. Cl.$^2$ ............................................. C07C 21/02
[52] U.S. Cl. ............................ 260/656 R; 260/659 A; 260/DIG. 42
[58] Field of Search ..................................... 260/656 R

[56] References Cited

U.S. PATENT DOCUMENTS

3,557,229   1/1971   Riegel .............................. 260/656 R

FOREIGN PATENT DOCUMENTS

1574705   6/1969   France .................................. 260/656 R

*Primary Examiner*—C. Davis
*Attorney, Agent, or Firm*—Louis E. Marn; Elliot M. Olstein

[57] ABSTRACT

1,2-dichlorethane is dehydrochlorinated by direct contact with a molten salt including the higher and lower valent forms of a multivalent metal chloride and generally also the oxychloride of the metal with ethane being present to increase selectivity to vinyl chloride.

17 Claims, 2 Drawing Figures

DEHYDROCHLORINATION OF 1,2-DICHLOROETHANE

This is a continuation, of application Ser. No. 437,985, filed Jan. 30, 1974, and now abandoned.

This invention relates to the production of vinyl chloride, and more particularly, to improved dehydrochlorination of 1,2-dichloroethane to vinyl chloride.

In U.S. Application Ser. No. 94,536 filed on Dec. 2, 1970, and now U.S. Pat. No. 3,935,288 there is described a process for dehydrochlorinating 1,2-dichloroethane to vinyl chloride by the use of molten salts. In accordance with the described process, 1,2-dichloroethane is dehydrochlorinated by direct contact with a melt containing the higher and lower valent forms of a multivalent metal chloride, with the melt optionally including the corresponding oxychloride, at high conversion and higher selectivity. It has been recently found that in the case where the melt includes the oxychloride, the selectivity to vinyl chloride is lower than the case in which the melt does not include the oxychloride. Furthermore, in many cases, the 1,2-dichloroethane employed as feed is recovered from the clorination effluent produced in an overall process for the production of vinyl chloride, as described in U.S. Application Ser. No. 153,374, filed on June 15, 1971 and now U.S. Pat. No. 3,937,744. The recovered 1,2-dichloroethane may include unsaturated chlorinated hydrocarbons, such as trichloroethylene, which may function as dehydrochlorination inhibitors and thereby decrease selectivity to vinyl chloride.

Accordingly, an object of the present invention is to provide an improved process for dehydrochlorinating 1,2-dichloroethane.

Another object of the present invention is to provide an improved process for producing vinyl chloride which includes dehydrochlorination of 1,2-dichloroethane.

A further object of the present invention is to provide a process for dehydrochlorinating 1,2-dichloroethane by the use of molten salts including oxychloride with improved vinyl chloride selectivity.

These and other objects of the present invention should be more readily apparent from reading the following detailed description thereof.

In accordance with the present invention, 1,2-dichloroethane is dehydrochlorinated by direct contact with a molten salt containing a multivalent metal chloride in its higher and lower valence state the contacting being effected in the presence of ethane in that the presence of ethane has been found to improve the overall selectivity to vinyl chloride.

More particularly, the ethane is present in an amount to provide a weight ratio of ethane to 1,2-dichloroethane from about 0.01:1 to about 0.15:1, and preferably from about 0.015:1 to about 0.10:1. The use of ethane in amounts lower than those hereinabove described does not provide the desired improvement in selectivity to vinyl chloride, and the use of ethane in amounts greater than those hereinabove described results in a decrease in vinyl chloride selectivity and/or 1,2-dichloroethane conversion.

Although the present invention is not bound by any theory, it is believed that the addition of ethane functions to reduce substitutive chlorination of dichloroethane which results in an increase selectivity to vinyl chloride. It is further believed that the addition of ethane functions, in part, to inhibit the increase of cupric chloride concentration of the melt through the dehydrochlorination reaction zone which could result from interaction between any oxychloride present in the melt and hydrogen chloride released during the dehydrochlorination.

The melts employed in the dehydrochlorination include the higher and lower valent forms of a chloride of a multivalent metal, i.e., a metal having more than one positive valence state such as manganese, iron, copper, cobalt and chromium, preferably copper. In the cases of higher melting multivalent metal chloride, such as copper chlorides, a metal salt melting point depressant which is non-volatile and resistant to the action of oxygen at the process conditions, such as a chloride of a univalent metal; i.e, a metal having only one positive valence state, is added to the multivalent metal chloride to form a molten salt mixture having a reduced melting point. The univalent metal chlorides, are preferably alkali metal chlorides, such as potassium and lithium chlorides in particular, but it is to be understood that other metal chlorides and mixtures thereof, such as the heavy metal chlorides, i.e., heavier than copper, of Groups I, II, III and IV of the Periodic Table; e.g., zinc, silver and thallium chloride, may also be employed. The metal chloride melting point depressant is added in an amount sufficient to maintain the salt mixture as a melt at the reaction temperatures, and is generally added in an amount sufficient to adjust the melting point of the molten salt mixture to a temperature of below about 500° F. In the case of a salt mixture of copper chlorides and potassium chloride, the composition of the melt ranges between about 20% to about 40%, preferably about 30%, by weight, potassium chloride, with the remainder being copper chlorides. it is to be understood, however, that in some cases the catalyst melt may have a melting point higher than 500° F., provided the catalyst remains in the form of the melt throughout the processing steps. It is further to be understood that the melt may contain a mixture of multivalent metal chlorides or other reaction promoters. It is also to be understood that in some cases, metal chloride may be maintained in molten form without a melting point depressant.

In accordance with a preferred embodiment, the molten salt used in the dehydrochlorination further includes the oxychloride of the multivalent metal in that the oxychloride reacts with the hydrogen chloride liberated during the dehydrochlorination, as represented by the following equation using copper oxychloride as a representative oxychloride:

$$CuOCuCl_2 + HCl \rightarrow 2CuCl_2 + H_2O \quad (1)$$

In this manner, the effluent will have reduced amounts of hydrogen chloride (the effluent includes equilibrium amounts of hydrogen chloride). The oxychloride is preferably present in an amount to react with essentially all of the hydrogen chloride produced in the dehydrochlorination.

The ethane which is present during the dehydrochlorination reaction may be chlorinated in part or in its entirety to chlorinated hydrocarbons (vinyl chloride, ethyl chloride, dichloroethanes, etc.) as a result of the chlorinating ability of the molten salt.

The dehydrochlorination is generally effected at temperatures from about 700° F. to about 1200° F., preferably from about 750° F. to about 1000° F., although the temperatures could be as low as 575° F., and at pressures from about 1 to about 20 atmospheres. The contacting of feed and melt is generally effected in a countercurrent fashion, preferably with the feed as a continuous vapor phase, at residence times from about 1 to about 60 seconds, although longer residence times may be employed.

The dehydrochlorination process of the present invention is preferably employed as part of an overall process for producing vinyl chloride from ethane and/or ethylene by the use of molten salts. More particularly, ethane and/or ethylene is contacted with a melt containing the multivalent metal chloride in its higher and lower valence state, with the molten salt mixture preferably also containing the oxychloride of the metal, with the contacting preferably also being effected with hydrogen chloride and/or chlorine to produce an effluent containing vinyl chloride and 1,2-dichloroethane. The vinyl chloride is recovered as product and the 1,2-dichloroethane is dehydrochlorinated by direct contact with the molten salt containing the higher and lower valent metal chloride, and preferably also including the oxychloride of the multivalent metal, in the presence of ethane as hereinabove described, to produce a dehydrochlorination effluent containing vinyl chloride.

In accordance with a preferred embodiment of the present invention, a molten salt mixture containing copper chlorides and a melting point depressant (preferably in an amount from 20 to 40 weight percent of the melt with the melting point depressant being preferably potassium chloride, with the remainder of the melt being copper chlorides) is contacted in a first reaction zone with molecular oxygen to produce copper oxychloride. The cupric chloride content of the melt is generally at least about 16%, by weight, of the melt, and generally from about 18% to about 50%, by weight, in order to provide sufficient cupric chloride for the subsequent chlorination and dehydrochlorination reactions. It is to be understood, however, that lower amounts of cupric chloride may be employed by increasing salt circulation rates and residence times. As a result of the various reactions which occur during the chlorination and dehydrochlorination steps, the cupric chloride content of the melt does not significantly vary through the various reaction zones. The molecular oxygen is preferably introduced in an amount, and at a rate, to provide a molten salt mixture containing from about 0.5% to about 5.5%, preferably from about 1% to about 3%, all by weight, of copper oxychloride. It is to be understood that minor amounts of chlorine and/or hydrogen chloride could also be introduced into the first reaction zone, but in accordance with this preferred embodiment, the major portion of the chlorine and/or hydrogen chloride is added to the chlorination zone.

The molten salt mixture, now containing copper oxychloride, is circulated to a second reaction zone (chlorination zone) wherein the molten salt is contacted with ethane and/or ethylene, preferably ethane, and chlorine and/or hydrogen chloride as fresh feed, in addition to recycle unconverted ethane (if employed as feed) and recycle ethyl chloride and unreacted ethylene or that generated as reaction intermediate. The recycle, may also include 1,1-dichloroethane and/or dichloroethylene.

The effluent from the second zone includes vinyl chloride, 1,2-dichloroethane, ethyl chloride, ethane, ethylene, and heavier chlorinated hydrocarbons; for example, one or more of the following: trichloroethylene, tetrachloroethylene, trichloroethanes and tetrachloroethane. The effluent also includes water vapor and equilibrium amounts of hydrogen chloride.

The reaction effluent is passed to a separation and recovery zone wherein various components are recovered. Ethyl chloride, ethane and ethylene are recovered for ultimate conversion to vinyl chloride. The recovered 1,2-dichloroethane is introduced into a dehydrochlorination zone (third reaction zone) wherein the 1,2-dichloroethane is contacted with molten salt from the first (the salt includes oxychloride), the second zone or both zones in the presence of ethane to effect dehydrochlorination of 1,2-dichloroethane to vinyl chloride. As a result of the chlorinating ability of the molten salt all or a portion of the ethane is converted to chlorinated products, as described with reference to the second reaction zone. The effluent from the dehydrochlorination reaction zone is introduced into a separation and recovery zone to recover vinyl chloride reaction product and other components for ultimate utilization thereof for the production of vinyl chloride.

The ethane utilized in the dehydrochlorination reaction zone may be either fresh feed or recycle ethane recovered from the chlorination (second reaction zone) effluent or a combination thereof. It is to be understood that the source of ethane is immaterial to the present invention, provided the ethane is employed for the dehydrochlorination as hereinabove described.

The chlorination in the presence of the melt (second reaction zone) may be effected at conditions, as hereinabove described with reference to the dehydrochlorination in the presence of molten salt. The production of oxychloride is generally effected at temperatures of 600°-900° F., although higher temperatures may be employed. The preferred oxychloride production temperature is from 750°-870° F.

The overall process for producing vinyl chloride from ethane and/or ethylene by the use of molten salts, including dehydrochlorination of 1,2-dichloroethane by the use of molten salts, is described in Application Ser. No. 153,374 filed on June 15, 1971, which is hereby incorporated by reference. The present invention is an improvement with respect to such a process in that dehydrochlorination selectivity to vinyl chloride is improved by use of ethane in the dehydrochlorination zone, as hereinabove described.

Figure 2:
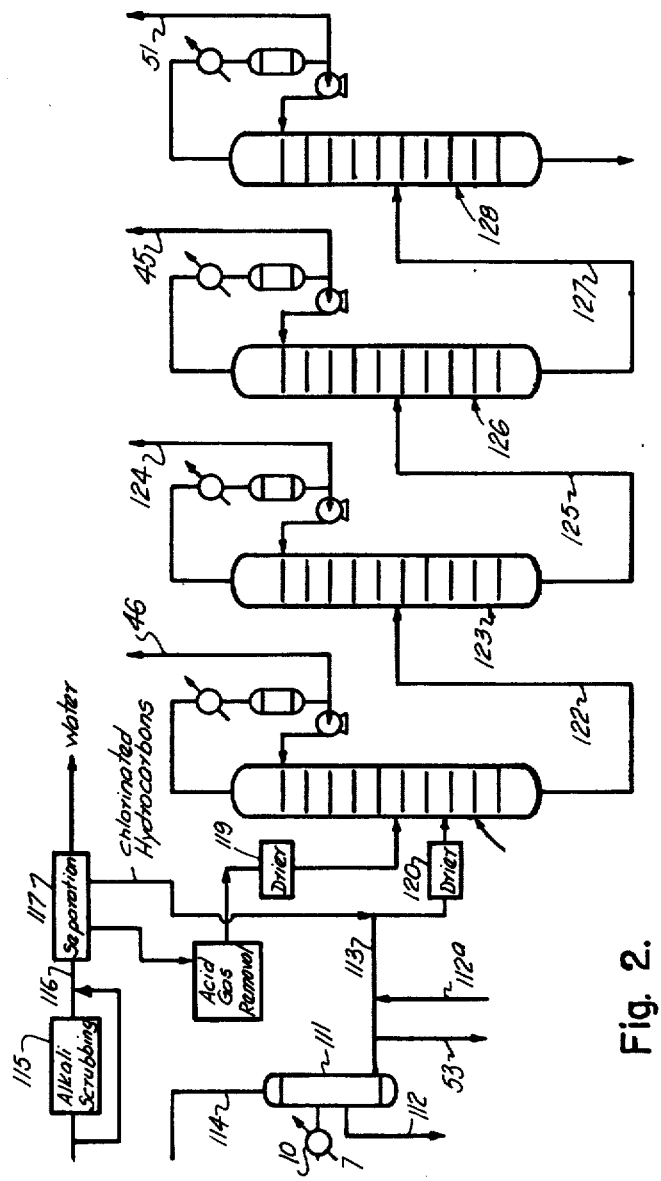

The invention will now be further described with reference to embodiments thereof illustrated in the accompanying drawings wherein:

FIG. 1 is a simplified schematic process flow diagram of the reaction portion of an embodiment of the invention; and FIG. 2 is a simplified schematic process flow diagram of the separation and recovery portion for recovering reactions products.

It is to be understood that the molten copper chloride salts are highly corrosive and, accordingly, the processing equipment must be suitably protected; i.e., the reactors may be lined with ceramic. Similarly, if pumps are used for transporting the molten salts they must also be protected. The molten salts, however, are preferably transferred between the reactors by the use of gas lifts, as shown in the art.

Referring now to FIG. 1, a molten chloride salt, such as a mixture of potassium chloride, cuprous chloride and cupric chloride in line 10 is introduced into the top of the reaction portion of an oxidation vessel 11 maintained, as hereinabove described, at temperatures and pressures suitable for oxidizing the molten salts. A compressed oxygen-containing gas, such as air, in line 12 is introduced into the bottom of vessel 11 and is passed in countercurrent contact to the descending molten salt, resulting in oxidation of the salt to produce copper oxychloride with the concurrent evolution of heat. In addition, a combustion effluent resulting from the combustion of heavier chlorinated by products, such as tri- and tetrachloroethanes and ethylenes and including hydrogen chloride and/or chlorine may be introduced into vessel 11 through line 12a, as described in British Patent Specification No. 1,205,831.

An effluent gas, comprised essentially of the nitrogen introduced with the air, (the effluent would also include combustion products, if a combustion effluent is introduced through line 12a) rises into the top of the vessel 11 wherein the effluent gas is combined with lift gas, as hereinafter described, introduced through line 13. The effluent gas is directly contacted in the top of vessel 11 with a spray of quench liquid in particular aqueous hydrogen chloride introduced through line 14 to cool the effluent gas and thereby eliminate any vaporized and entrained salts therefrom. The effluent gas, now containing vaporized quench liquid, is withdrawn from vessel 11 through line 15 and introduced into a direct contact quench tower 16, of a type known in the art wherein the effluent gas is cooled by direct contact with a suitable quench liquid, in particular aqueous hydrogen chloride, introduced through line 17 to thereby remove vaporized quench liquid from the effluent gas.

The quench liquid is withdrawn from the bottom of tower 16 through line 18 and a first portion passed through line 14 for quenching the effluent gas in vessel 11. A second portion of the quench liquid is passed through line 19, containing a cooler 21, for introduction into the quench tower 16 through line 17.

An effluent gas, comprised essentially of nitrogen, is withdrawn from quench tower 16 through line 22 and a portion thereof purged through line 23. The remaining portion of the nitrogen effluent gas is compressed in compressor 24 and the temperature thereof regulated in heat exchanger 63 prior to passage through lines 25 and 26 for use as a lift gas for transporting molten salt, as hereinafter described.

The molten salt, now containing copper oxychloride, is withdrawn from the bottom of vessel 11 through line 31 and lifted by the lift gas in line 25 into a separation vessel 32 positioned adjacent the top of the reaction portion of a reaction vessel 33. In separator 32, the molten salt is separated from the lift gas, with the separated lift gas being withdrawn through line 35 and combined with lift gas from the oxidation reactor for introduction into the quenching portion of vessel 11 through line 13.

The reaction vessel 33 is divided into two separate reaction sections, 41 and 42 with reaction section 41 functioning as a chlorination reaction zone and section 42 as a dehydrochlorination reaction zone. The molten salt, containing cuprous chloride, cupric chloride, copper oxychloride and the potassium chloride melting point depressant, from separator 32, in line 34, is introduced into both reaction sections 41 and 42.

Fresh feed chlorine and/or hydrogen chloride is introduced into the bottom of section 41 through 43 and all or a portion of the fresh feed ethane and/or ethylene, preferably ethane, in line 44 is combined with a recycle chlorinated hydrocarbon stream comprised of ethyl chloride and also some dichloroethylene, and 1,1-dichloroethane, in line 45, and recycle ethane and ethylene, in line 46, for introduction into the bottom of section 41 through line 47. It is to be understood that the various streams could be separately introduced.

The reaction section 41 is operated at the temperatures and pressures hereinabove described, to produce an effluent which contains as combined reaction product, vinyl chloride and 1,2-dichloroethane. The effluent also includes ethyl chloride, some 1,1-dichloroethane, dichloroethylenes, ethane, ethylene, water vapor, some hydrogen chloride and heavier chlorinated hydrocarbons.

1,2-dichloroethane feed in line 51 which may also include some heavier close boiling chlorinated hydrocarbons, such as trichloroethylene and ethane in line 51a is introduced into the bottom of reaction section 42 and countercurrently contacts the descending molten salt. It is to be understood that the ethane and 1,2-dichloroethane could be introduced through the same line. As a result of such contact, the 1,2-dichloroethane is dehydrochlorinated to vinyl chloride, and hydrogen chloride, which as hereinabove noted, reacts with the oxychloride present in the melt. In addition, all or a portion of the ethane is converted to chlorinated product.

It is to be understood that the dehydrochlorination could be effected in a separate vessel, instead of a separate section of vessel 33.

The reaction effluent from the chlorination section 41 is combined with the reaction effluent from dehydrochlorination reaction section 42 in quenching section 52 wherein the effluent gas is directly contacted with a spray of quench liquid, in particular one or more of the chlorinated hydrocarbons produced in reaction section 41, introduced through line 53 to cool the effluent gas and thereby eliminate vaporized and entrained salts therefrom.

The effluent gas, now containing vaporized quench liquid, is withdrawn from vessel 33 through line 54 and introduced into a separation and recovery section (FIG. 2) for recovery of the various components.

A molten salt obtained from sections 41 and 42 is withdrawn from the bottom of reactor 33 through line 61 and lifted by lift gas in line 26 into a separation vessel 62 positioned adjacent the top of reactor 11. In separator 62, the molten salt is separated from the lift gas and introduced through line 10 into vessel 11. The lift gas is withdrawn from separator 62 through line 64 and combined with the lift gas in line 35 for introduction into the top quenching section of vessel 11 through line 13.

Referring now to FIG. 2, the reaction effluent in line 54 is cooled in condenser 110, primarily to condense a portion of the water therefrom (the condensed water would also contain hydrogen chloride, if present), the aforesaid cooling also resulting in the condensation of chlorinated hydrocarbons, including the chlorinated hydrocarbons used as quench liquid. The condensed water and chlorinated hydrocarbons are separated in a separator 111, with a water phase being withdrawn through line 112 and a chlorinated hydrocarbon phase being withdrawn through line 113. A portion of the chlorinated hydrocarbons in line 113 is recycled through line 53 as quench liquid for reactor 33. Alternatively, all of such chlorinated hydrocarbons, if required, may be recycled as quench liquid. The water phase in line 112 is stripped of entrained and dissolved chlorinated hydrocarbon in a stripping column (not shown)

and the recovered chlorinated hydrocarbons (from the stripping column) in line 112a are combined with the chlorinated hydrocarbons in line 113. Depending on the amount of hydrogen chloride present in the water, the water may also be treated to recover hydrogen chloride or a concentrated solution of hydrogen chloride.

The remaining portion of the gaseous effluent in line 114 is optionally passed through an alkali scrubbing zone, of a type known in the art, schematically indicated as 115, to remove any remaining hydrogen chloride therefrom.

The gaseous effluent from the alkali scrubbing zone 115, if used, in line 116 is generally passed through a further cooling and separation zone, schematically indicated as 117, to condense further water and chlorinated hydrocarbons therefrom; an acid gas removal zone 118, of a type known in the art, to remove any acid gas, primarily carbon dioxide, and a drier 119, and introduced into a fractional distillation column 121. The chlorinated hydrocarbons in line 113 and chlorinated hydrocarbons separated in zone 117 are combined and dried in drier 120 for introduction into column 121. Alternatively, if required, a portion of the chlorinated hydrocarbons recovered in zone 117 may be recycled as quench liquid to reactor 33. The water separated in zone 117 may be passed to a stripping column to recover any chlorinated hydrocarbons with such recovered chlorinated hydrocarbons also being introduced into column 121.

The column 121 is operated at temperatures and pressures to produce a gaseous overhead comprised of ethane and ethylene, which is recovered in line 46 and recycled to reaction section 41.

A chlorinated hydrocarbon bottoms withdrawn from column 123 through line 125 is introduced into a fractional distillation column 126 operated at temperatures and pressures to recover as overhead 1,1-dichloroethane and lower boiling chlorinated hydrocarbons, in particular ethyl chloride and dichloroethylenes. The overhead from column 126, comprised essentially of 1,1-dichloroethane, dichloroethylenes and ethyl chloride is recovered in line 45 for recycle to reactor 33. If desired, the overhead from column 126 may be further fractionated to produce a recycle stream essentially free of dichloroethylenes.

A bottoms of 1,2-dichloroethane and heavier chlorinated products is withdrawn from column 126 through line 127 and introduced into fractional distillation column 128 operated at temperatures and pressures to produce an overhead of 1,2-dichloroethane. The 1,2-dichloroethane overhead recovered in column 128 is passed to the dehydrochlorination section 42 through line 51. The bottoms stream from distillation column 128 is comprised of one or more of the following: trichloroethane, trichloroethylene, tetrachloroethane and tetrachloroethylene. This bottoms stream may be combusted as described in British Patent Specification No. 1,205,831, and the combustion product passed to oxidation vessel 11 to recover chlorine values therefrom.

Although the invention has been particularly described with respect to an embodiment in which oxychloride is present in the melt employed in the dehydrochlorination reaction zone, the present invention may also be employed in cases where there is no oxychloride present in that the 1,2-dichloroethane feed to the dehydrochlorination reaction zone, in such a case, may include a dehydrochlorination inhibitor, such as trichloroethylene. The addition of ethane to the dehydrochlorination reaction zone, as hereinabove described, minimizes the adverse effect on selectivity to vinyl chloride which could result from the presence of a dehydrochlorination inhibitor.

The invention will be further described with respect to the following example, but the scope of the invention is not to be limited thereby.

EXAMPLE I

A molten salt comprised of 17.1 wt. % cupric chloride; 51.8 wt. % cuprous chloride; 0.2 wt. % copper oxychloride; and 30.9 wt. % potassium chloride is countercurrently contacted with a feed comprised of 90.6 mole % of a 1,2-dichloroethane blend and 9.4 mole percent of ethane, at a temperature of 849° F. and a residence time of 8.7 seconds. The 1,2-dichloroethane blend has the following composition:

| DCE blend | mole % |
| --- | --- |
| 1,1,1 $C_2H_3Cl_3$ | 0.6 |
| $CCl_4$ | 1.3 |
| 1,2 $C_2H_4Cl_2$ | 78.3 |
| $C_2HCl_3$ | 11.1 |
| 1,1,2 $C_2H_3Cl_3$ | 4.5 |
| $C_2Cl_4$ | 4.2 |
| | 100.0 |

The vinyl chloride selectivity is 90.4 mole percent, and the 1,2-dichloroethane conversion is 80 mole percent, notwithstanding the presence of oxychloride in the melt and the use of a high proportion of trichloroethylene in the feed which would be expected to inhibit dehydrochlorination.

EXAMPLE II

A molten salt comprised of 16.5 wt. % cupric chloride; 52.6 wt. % cuprous chloride; 0.2 wt. % copper oxychloride; and 30.7 wt. % potassium chloride is countercurrently contacted with a feed comprised of 84.5% mole % of the 1,2-dichloroethane blend of Example I and 15.5 mole percent of ethane, at a temperature of 850° F. and a residence time of 7 seconds. The vinyl chloride selectivity is 91.8 mole percent, and the 1,2-dichloroethane conversion is 79.7 mole percent.

The present invention is particularly advantageous in that 1,2-dichloroethane can be dehydrochlorinated to vinyl chloride at conversions in excess of 70 percent while maintaining selectivity to vinyl chloride of at least about 80 percent, (and generally selectivites of greater than 90% can be achieved), notwithstanding the presence of oxychloride in the melt and/or the presence of a dehydrochlorination inhibitor, such as trichloroethylene, in the 1,2-dichloroethane feed.

Numerous modifications and variations of the present invention are possible in light of the above teachings and therefore, within the scope of the appended claims, the invention may be practised otherwise than as particularly described.

What is claimed is:

1. In a process for dehydrochlorinating 1,2-dichloroethane to vinyl chloride by direct contact with a molten salt containing the higher and lower valent chlorides of a multivalent metal, wherein during said dehydrochlorination, there is present at least one of an oxychloride of the multivalent metal in molten form and trichloroethylene, the improvement comprising:

effecting said contacting in the presence of ethane to provide an ethane to 1,2-dichloroethane weight ratio from about 0.01:1 to about 0.15:1 to increase selectivity to vinyl chloride.

2. The process of claim 1 wherein said melt includes the oxychloride of the multivalent metal.

3. The process of claim 1 wherein the multivalent metal chloride is selected from the group consisting of the chlorides of copper, chromium, cobalt, iron, manganese and mixtures thereof.

4. The process of claim 1 wherein the multivalent metal chloride is copper chloride.

5. The process of claim 4 wherein the contacting is effected at a temperature from 700° F. to 1200° F.

6. The process of claim 4 wherein the melt further includes copper oxychloride.

7. The process of claim 6 wherein the contacting is effected at a temperature from about 700° F. to about 1200° F.

8. The process of claim 7 wherein the melt further includes, as a melting point depressant, a member selected from the group consisting of the alkali metal chlorides and the heavy metal chlorides and mixtures thereof.

9. The process of claim 8 wherein the ethane to 1,2-dichloroethane weight ratio is from about 0.015:1 to about 0.10:1.

10. The process of claim 8 wherein the dehydrochlorination inhibitor, trichloroethylene is present during the dehydrochlorination.

11. A process for producing vinyl chloride, comprising:
(a) contacting in a first reaction zone hydrocarbon selected from the group consisting of ethane, ethylene and mixtures thereof with a member selected from the group consisting of chlorine, hydrogen chloride and mixtures thereof and a melt comprising the higher and lower valent chlorides of a multivalent metal and the oxychloride of the multivalent metal to produce a first effluent containing vinyl chloride and 1,2-dichloroethane;
(b) recovering vinyl chloride and 1,2-dichloroethane from the first effluent; and
(c) dehydrochlorinating recovered 1,2-dichloroethane to vinyl chloride by direct contact with a melt containing the higher and lower valent chlorides of a multivalent metal and the oxychloride of the metal, said contacting being effected in the presence of ethane in an amount to provide an ethane to 1,2-dichloroethane weight ratio from about 0.01:1 to about 0.15:1.

12. The process of claim 11 wherein the multivalent metal chloride employed in steps (a) and (c) is selected from the group consisting of the chlorides of copper, chromium, cobalt, iron, manganese and mixtures thereof.

13. The process of claim 12 wherein the multivalent metal chloride is copper chloride.

14. The process of claim 13 wherein the contacting of steps (a) and (c) is effected at a temperature from 700° F. to 1200° F.

15. the process of claim 14 wherein the melt further includes, as a melting point depressant, a member selected from the group consisting of the alkali metal chlorides and the heavy metal chlorides and mixtures thereof.

16. The process of claim 15 wherein the ethane to 1,2-dichloroethane weight ratio is from about 0.015:1 to about 0.10:1.

17. The process of claim 15 wherein the 1,2-dichloroethane is recovered from the first effluent in combination with trichloroethylene as an impurity whereby trichloroethylene is present during the dehydrochlorination of 1,2-dichloroethane.

* * * * *